(12) United States Patent
Maublant

(10) Patent No.: US 6,603,124 B2
(45) Date of Patent: Aug. 5, 2003

(54) APPARATUS FOR DETECTING AND LOCATING A RADIOACTIVE SOURCE EMITTING GAMMA RAYS AND USE OF SAID APPARATUS

(76) Inventor: Jean Maublant, 53 Cours Sablon, F-63000 Clermont-Ferrand (FR)

(*) Notice: Subject to any disclaimer, the term of this patent is extended or adjusted under 35 U.S.C. 154(b) by 19 days.

(21) Appl. No.: 10/026,127

(22) Filed: Dec. 21, 2001

(65) Prior Publication Data

US 2003/0111611 A1 Jun. 19, 2003

Related U.S. Application Data

(63) Continuation of application No. PCT/FR00/01746, filed on Jun. 22, 2000.

(30) Foreign Application Priority Data

Jun. 22, 1999 (FR) .............................................. 99 08115

(51) Int. Cl.[7] .................................................. G21K 1/02
(52) U.S. Cl. .............................. 250/363.1; 250/363.02; 250/363.04
(58) Field of Search ........................ 250/363.1, 363.02, 250/370.09, 493.1, 252.1; 378/147, 145, 98.8

(56) References Cited

U.S. PATENT DOCUMENTS

| | | | | |
|---|---|---|---|---|
| 2,942,109 A | | 6/1960 | Bell et al. ................... | 250/71.5 |
| 3,794,840 A | | 2/1974 | Scott .......................... | 250/363 |
| 4,200,799 A | * | 4/1980 | Saito ........................... | 378/13 |
| 5,694,933 A | * | 12/1997 | Madden et al. ............. | 600/431 |
| 5,777,332 A | * | 7/1998 | Lonn et al. ............ | 250/363.04 |
| 6,285,028 B1 | * | 9/2001 | Yamakawa ............. | 250/370.09 |
| 6,285,739 B1 | * | 9/2001 | Rudin et al. ............... | 378/98.8 |
| 2001/0056234 A1 | * | 12/2001 | Weinberg ................... | 600/436 |

* cited by examiner

Primary Examiner—David Porta
Assistant Examiner—Christine Sung
(74) Attorney, Agent, or Firm—Heslin Rothenberg Farley & Mesiti P.C.; Victor A. Cardona, Esq.

(57) ABSTRACT

This invention concerns a device for detecting and locating a radioactive source emitting gamma rays, characterized in that it comprises: first means for determining the direction of the gamma radiation emitting source relative to the centre of the detector comprising: gamma radiation sensing means; a plurality of means for evaluating the gamma radiation flux; means analyzing the gamma radiation flux for determining the direction of-the radiation source; second means for directing the radioactive emitting source comprising mechanical means for causing the device to move, so as to bring its centerline nearer the gamma radiation emitting source; means physically representing the device centerline.

12 Claims, 2 Drawing Sheets

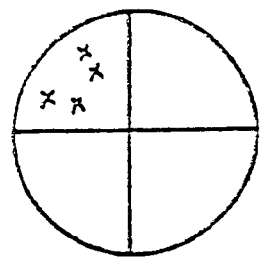
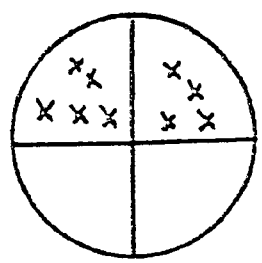
FIG.3
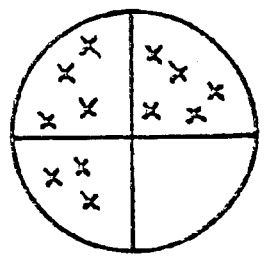
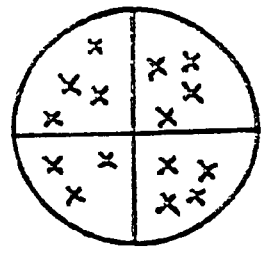

APPARATUS FOR DETECTING AND LOCATING A RADIOACTIVE SOURCE EMITTING GAMMA RAYS AND USE OF SAID APPARATUS

CROSS REFERENCE TO RELATED APPLICATIONS

This application is a continuation of International Application No. PCT/FR00/01746, filed Jun. 22, 2000 and published in French, as WO 00/79301 on Dec. 28, 2000. PCT/FR00/01746 claimed the priority of French patent application 99.08115, filed Jun. 22, 1999. The priorities of both applications are claimed herein and the entire disclosures are hereby incorporated herein by reference.

The invention relates to an apparatus for detecting and locating a radioactive source emitting gamma rays. It also relates to the use of the apparatus.

In the rest of the description, the detection apparatus of the invention applies more particularly, but not exclusively, to the detection of lymph nodes, some of which by fixing an in situ injected radioactive substance are capable of characterizing the extension of a tumor, especially in the case of breast cancer or skin cancer (melanoma).

However, other applications of the apparatus may be envisaged, such as the search for lost radioactive sources, the drilling of a material based on information available on its other face and, more widely, the detection and location of an almost point-like radioactive source through a medium that does not completely absorb the gamma rays that it emits, without this being restrictive.

Primary cancers firstly exhibit a local stage followed somewhat later by secondary sites. The extension process starts even before the clinical manifestations of dissemination are detectable. The first anatomical structures attacked outside the primary tumor are generally the lymph nodes. Thus, one cancer treatment consists in ablating the lymph nodes of the region in question. The purpose of such an operation is not only to remove possible secondary sites but also to diagnose possible metastasic dissemination, thus making it possible to propose the indication of a complementary medical treatment.

In the Particular case of breast cancer, the surgical treatment consists, apart from removing the primary tumor, in also removing the lymph nodes located in the axillary hollow, this operation being called "lymph node curage", and then in carrying out a histological analysis of the lymph nodes removed.

Such an operation is a major source of functional sequela for the patient. First of all, the lymphatic engorgement resulting from removal of the lymphatic system draining the major part of the upper limb generates a pathology called lymphoedema or "fat arm" syndrome causing as much a functional impediment as unsightliness. Furthermore, it turns out that during curage the branches of the first intercostal nerves present in the axillary region are cut, thus leading to the appearance of sensitive disorders. Motor disorders of the shoulder also appear.

Furthermore, and above all, it turns out -hat the lymph nodes removed during axillary curage do not always prove, by histological analysis, to be invaded. It should be noted, in particular, that in the case of tumors less than or equal to 10 mm in size, only 6% of the lymph nodes removed are invaded. In other words, 95% of curages carried out are in fact unnecessary.

This is the reason why a number of techniques have been developed to try to detect preoperatively and/or preoperatively, and then to remove, only the lymph node or nodes likely to be attacked during the secondary extension of a primary tumor.

Thus, in a case of the treatment of a melanoma, it has been found that the first, relay node draining the melanoma (called the sentinel node) is capable of fixing a dye, particularly patent blue.

It has been demonstrated that the absence of invasion of the sentinel node corresponds in almost 100% of cases to the absence of invasion of the other nodes. It therefore becomes possible, by carrying out an extemporaneous analysis of the sentinel node, once identified and then removed, to decide during intervention whether or not to continue the lymph node curage.

However, according to this technique, since identifying the sentinel node is strictly visual, it is necessary to dissect the tissues in the region where it is assumed the sentinel node is. However, since the sentinel node has no perfectly defined location from the anatomical standpoint, this search is not simple and may prove to be lengthy and relatively impairing.

To solve this problem, it has been proposed to replace the dye with a radioactive substance. Detection of the sentinel node is then performed by one of two techniques, respectively:
   either by scintigraphic imaging (lymphoscinti-graphy) using a scintillation camera;
   or using a peroperative detection probe.

It turns out that scintigraphic imaging of lymph nodes, although validated in the display of nodes in non-cancerous pathology, is poorly suited to the specific detection of the sentinel node.

This is because, owing to its imposing weight (more than 1 tonne), the imaging apparatus is not transportable, so that the examination has to be performed preoperatively and elsewhere than in the room where said operation is being carried out, thus complicating the planning organization for the various parties involved.

Moreover, and above all, locating is performed by means of skin marking guided by a radioactive source brought into correspondence with the hyperfixing area on the image. Consequently, this mark is necessarily imprecise since;
   firstly, it depends on how the head of the camera is angled;
   secondly, it is often difficult to mark the skin accurately in a soft and not easily accessible region;
   and finally, the surgeon cannot check in real time the well-foundedness of the skin mark.

At the same time, the angle of incidence of the incision may be different from that of the imaging, resulting in a location error which is all the greater the deeper the node.

In other words, the scintillation camera allows only coarse pre-locating of the position of the node during the preoperative stage.

On the other hand, the detection probe is a small piece of equipment, which can therefore be manipulated manually. This probe detects the gamma photons emitted by a radioactive source and allows audible location of said source placed within the beam angle of its collimator.

Technically, the detection probe includes a collimator consisting of a single hole, a scintillating crystal, a photomultiplier with a single anode, and associated electronic means for assessing, by a displayed numerical value or an audible signal, the intensity of the signal detected. However, this detection probe can only be used to assess the amount of radioactivity present in the field of view of its collimator, without being capable of specifying the precise direction in which the radioactive source lies.

In addition, it is very tricky to locate the node because of the very restricted angle of observation of the system and the large number of degrees of freedom in positioning. Moreover, because of the variability in the angle of incidence, and therefore in the thickness of the tissues through which the radiation emanating from the node passes, together with the inconstancy of the positioning, since the probe is hand-held, locating the nodes requites a great deal of time and sometimes proves to be fruitless.

In other words, the problem that the invention aims to solve is to provide an apparatus which allows preoperative and above all peroperative detection and precise location of a radioactive source, thus making it possible, for example in the case of the detection of lymph nodes, to avoid any unnecessary impairment in view of or during the surgical operation.

To solve this problem, the invention proposes an apparatus for detecting and locating a radioactive source emitting gamma rays.

This apparatus is characterized in that it comprises:
first means for determining the direction of the gamma-ray-emitting source with respect to the center of the detector;
a second means capable of pin-pointing the radioactive emission source.

In other words, the invention consists of a detection system making it possible during a surgical intervention to identify and precisely locate organs or tissues, and especially lymph nodes fixing a radioactive source emitting gamma rays.

Contrary to the technique of imaging using a scintillation camera, the objective is not to form a faithful image of the tissue or organ fixing the radicactive source, but to identify in which direction with respect to the center of the detector said source lies, so as to control the movement of the detector for the purpose of bringing this source opposite the central part of the detection area.

To achieve this objective, said first means comprise:
gamma-ray sensor means;
a plurality of means for measuring the gamma-ray flux;
means for analyzing the gamma-ray flux which are capable of determining the direction of the radioactive source.

In practice, the means for sensing the gamma rays consist of a collimator and a scintillating crystal capable of emitting a light signal under the effect of a gamma ray.

To sense the gamma rays emitted by the source, whatever their direction, the collimator has a central area comprising a plurality of mutually parallel channels which are perpendicular to the surface of said collimator.

Advantageously, the number of parallel channels is four.

According to another embodiment, the collimator furthermore has a peripheral area comprising a plurality of divergent channels making, with the channels of the central area, an angle which increases with their distance from the central area.

The specific structure of the collimator therefore makes it possible, because of its peripheral part, to detect the region of a possibly remote source without worrying about the precision in the location and, of a central part, to have a high special resolution so that the subsequent step of locking onto the direction of the tissue or organ fixing the radioactive source is precise.

Finally, It is conceivable to use an asymmetric collimator consisting of truncated divergent channels.

As already mentioned, the collimator is attached on its rear face to a scintillating crystal capable of emitting a light signal under the effect of gamma rays. In practice, however, this crystal consists of a thallium-activated cesium iodide or sodium iodide crystal. It has a thickness sufficient to stop a high proportion of the gamma photons to be detected. In practice, the thickness of the crystal is between 5 and 10 mm for detecting photons having an energy of 140 keV emitted by 99 m-technetium. The scintillating crystal has an overall round shape whose diameter depends on the photomultiplier used, this being described later.

As already mentioned, the precision in locating the impacts received by the peripheral part does not matter. All that it is required to know is whether the detector has to be moved more in one direction than in another.

To measure the flux of gamma rays picked up by the collimator, the apparatus of the invention includes a plurality of measuring means consisting of one or more single-anode photomultipliers capable of receiving the light signal emitted by the sensor means.

Advantageously, the number of single-anode photomultipliers is our.

In another advantageous embodiment of the apparatus, the means for measuring the gamma-ray flux consist of a multi-anode photomultiplier. The signal output by each anode would then be regarded as being equivalent to that output by the anode of a single-anode photomultiplier.

To determine precisely the direction of the radioactive source, the first means comprise, as already mentioned, means for analyzing the gamma-ray flux measured by the measuring means. The purpose of this analysis is to determine in what direction with respect to the center of the field of detection the radioactive source lies. The analysis indicates that the source is either offset in one particular direction or lies on the axis of the detector. The analysis is carried out by comparing the signals output by the measuring means and especially the photo-multipliers. This analysis uses electronic means to determine among the signals generated by each of the photomultipliers, or by a group of photomultipliers, which has the highest intensity.

In an advantageous embodiment, using the Anger camera principle, the signals output by the anode of each single-anode photomultiplier or each anode of the multi-anode photomultiplier are combined in order to form four signals coded in X and Y with respect to the center of the photomultiplier, these being denoted X−, X+, Y−, Y−, and the combination of which provides the X and Y coordinates of a given point. Thus the detected intensities are stored in four registers, for example North, South, East and West, according to the positivity of X and Y.

When only the data corresponding to the signals output by the central area of the crystal are to be processed, only the signals whose absolute value is less than a prefixed threshold are stored.

In an advantageous embodiment, the means for analyzing the measured flux are capable of taking into account all or only some of the intensities output by the measuring means, depending on the extent to which the intensities are almost uniform.

In other words, the data processing is carried out firstly on the basis of the signals output by the entire sensitive area of the crystal, making it possible to rapidly move the center of the detector closer to the source lying within the scan field and then, only from the central part of the crystal, making it possible to center the detector, more precisely, but more slowly, on the hot spot, whatever the sources lying in the rest of the scan field.

To enable the source of radioactive emission to be pinpointed, when the direction of gamma-ray emission has been detected and the emission of a signal has taken place, said second means of the detection apparatus of the invention comprise:

mechanical means capable of imparting a movement to the apparatus so as to move its central axis closer to the radioactive source emitting gamma rays;

means capable of defining the central axis of the apparatus.

In practice the mechanical means capable of imparting a movement to the apparatus comply with movement instructions as long as the analyzing means indicate that the central axis of the detector is not in correspondence with the source.

Moreover, the means capable of defining the central axis of the apparatus are in the form of a light ray.

According to an advantageous embodiment, said means are in the form of at least two coherent light sources generating narrow light beams, the intersection of which corresponds to the perpendicular at the center of the sensitive area of the collimator (center of the apparatus).

In one particular embodiment, the light source is positioned in such a way that the edge of the beam corresponds to a boundary of the region scanned by the collimator.

As already mentioned, the apparatus of the invention can be used to detect a human or animal tissue or organ fixing a gamma-ray emitting radioactive source.

In the case of skin cancer or breast cancer, the apparatus will be more particularly used for detecting lymph nodes which, by fixing a gamma-ray emitting radioactive source, testify to the secondary extension of the primary tumor.

The apparatus can also be used for the preoperative detection of an anomaly, such as for example breast microcalcifications, which microcalcifications will have been previously labelled by the in situ injection of a radioactive substance under radiographic or echographlc imaging control.

More generally, the apparatus of the invention may be used for detecting and locating a localized radioactive source through a medium which does not completely absorb he gamma rays that it emits.

Finally, the invention relates to a method of detecting a radioactive source emitting gamma rays fixed by a human or animal tissue or organ in which:

a radioactive substance emitting gamma rays is injected into the body;

the direction of the gamma-ray emitter is determined; characterized in that the direct-on determined is defined so as to pinpoint the source of radioactive emission.

The invention and the advantages which stem therefrom will become more clearly apparent from the following illustrative example in conjunction with the appended figures.

FIG. 3 s a representation of the various impacts detected by the photomultiplier via the surface of the collimator and converted into electrical signals.

Apparatus

Figure 1:
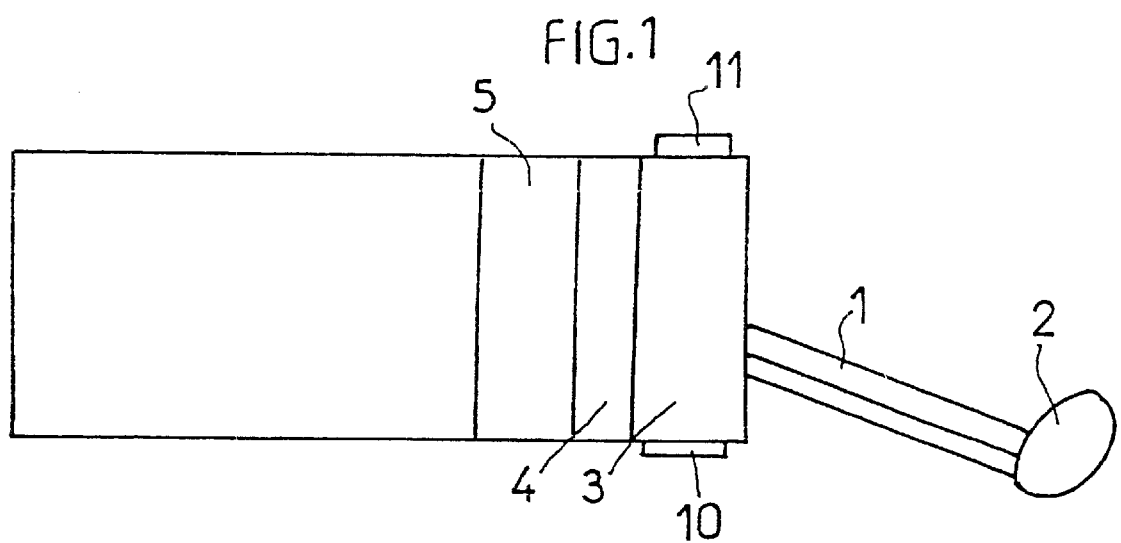
FIG. 1 is a schematic representation of the first means constituting the detection apparatus of the invention.
Figure 2:
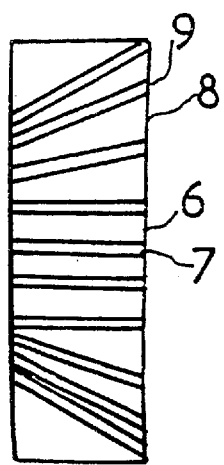
FIG. 2 is a section through the collimator along its central axis.

FIG. 1 shows schematically the first means of the detection apparatus of the invention. These consist of sensor means for sensing the garrma rays. (1) emitted by the source (2), a plurality of means for measuring the gamma-ray flux and means for analyzing the measured flux.

The sensor means consist of a collimator (3) which has a scintillating crystal (4) on its rear face.

Moreover, the plurality of means for measuring the flux of the gamma rays (1) are in the form of a multi-anode photomultiplier (5) having four anodes. To identify in which direction the radioactive source (2) lies with respect to the center of the detector, the collimator has:

a central area (6) comprising a plurality of mutually parallel channels (7) perpendicular to the surface of said collimator;

a peripheral area (8) comprising a plurality of divergent channels (9) which are at an angle with the channels (7) of the central area (6) which increases with their distance from said central area.

As already mentioned the photomultiplier has four anodes defining four sectors—North, South, East and West—with respect to the center of the photomultiplier. Thus, the intensities measured by the various sectors of the photomultiplier are analyzed in the form of four points coded in terms of X and Y with respect to the center of the photomultiplier, thus determining the coordinates of the impacts detected in the four North, South, East and West registers.

The apparatus also includes second means (not shown) capable of pin-pointing the radioactive emission source. These second means consist of mechanical means or imparting a movement to the apparatus and means capable of defining the central axis of the apparatus, especially in the form of a light ray.

Operation of the Apparatus

In this example, the detection apparatus is used to detect the sentinel node, labeled with 99 m technetium, especially within the context of breast cancer.

During the intervention, the detection apparatus is placed a few centimeters above the region within which the radioactive node probably lies.

In a first step, he means for analyzing the intensities measured by the photomultiplier process all of the signals output by the entire sensitive area of the crystal.

What is obtained is a number of impacts on the four anodes, these being converted into electrical signals by the photomultiplier. These impacts are distributed within the four—North, East, South and West—registers, as shown in FIG. 3. The apparatus is moved by the mechanical means in the direction in which lies that sector whose activity or flux is greater than a minimum background noise threshold measured beforehand. Likewise, if two sectors have an activity greater than the background noise, the apparatus is moved in the direction intermediate between the two sectors until the measured fluxes are almost the same. If three or four sectors have a greater activity, the apparatus then processes only the impacts obtained in the central area of the crystal.

To avoid having to reset the registers to zero at each movement of the apparatus, the setting-to-zero may take place at regular intervals, especially every two seconds. As already mentioned, the second step follows on automatically and is restricted to analyzing the central part of the crystal, thus making it possible to center the apparatus more precisely, but more slowly on the hot point, whatever the sources lying within the rest of the scan field.

As long as the values of the North, East, South and West registers are unequal, the mechanical movement means are activated for movement in the direction of the sector corresponding to the register containing the maximum value. The four cardinal registers are reset to zero at shorter time intervals than in the initial phase.

When the radioactive tissue or organ is in the center of the field, the values contained in the registers are equal to one another, which immobilizes the apparatus and generates a specific signal, for example an audible signal or a flashing light. However, it should be noted that the notion of equality between the register values, must take account of the fact that it results From the temporal accumulation of a number of radioactive disintegrations. These values are therefore subject to statistical fluctuations of the Poissonian type. It is therefore necessary to avoid any movement of the apparatus while it is in the central equilibrium position, and to define a difference threshold between the register below which it is probable that the equilibrium position has been achieved.

For this purpose, a fifth register, denoted sigma, contains the sum of the four others. Once equilibrium has been achieved, the central axis of the detector is defined by a light beam of the laser type emitted by the systems (10, 11) shown in FIG. 1. The light beam indicates, on the surface of the skin or on the visible surface of the targeted tissues, the direction of provenance of the source, that is to say the direction in which the radioactive node lies.

The system has the advantage of operating in real time, so that the light beam continuously indicates the direction in which the node lies, even in the case of possible displacement of the tissues pressed by the surgeon, for example when he makes an incision in the tissues, seals them, or changes the position of the retractors.

As already mentioned, the apparatus of the invention can be applied to the detection of any tissue or organ fixing a radioactive source.

This method of detection will be more particularly advantageous for the detection of sentinel nodes, especially within the context of breast cancers or The advantages of the invention are clearly apparent from the description.

The ability of the apparatus to precisely locate a radioactive source, so as to minimize the surgical intervention, should in particular be noted.

What is claimed is:

1. An apparatus for detecting and locating a radioactive source emitting gamma rays, comprising:
   gamma-ray sensor;
   a plurality of measuring means capable of receiving a light signal emitted by the sensor;
   analyzing means for comparing signals output by the measuring means in order to determine a direction in which the source is offset with respect to a detection axis;
   means for defining a central axis of the apparatus; and
   means for imparting a movement to the apparatus in response to movement instructions as long as the analyzing means indicate that the central axis of the apparatus is not in correspondence with the source.

2. The apparatus as claimed in claim 1, characterized in that the means for sensing the gamma rays consist of a collimator and a scintillating crystal capable of emitting a light signal under the effect of a gamma ray.

3. The apparatus as claimed in claim 2, characterized in that the collimator has a central area comprising a plurality of mutually parallel channels which are perpendicular to the surface of said collimator.

4. The apparatus as claimed in claim 3, characterized in that the central area has four channels.

5. The apparatus as claimed in claim 4 wherein the collimator furthermore has a peripheral area comprising a plurality of divergent channels making, with the channels of the central area, an angle which increases with their distance from the central area.

6. The apparatus as claimed in claim 3 wherein the collimator furthermore has a peripheral area comprising a plurality of divergent channels making, with the channels of the central area, an angle which increases with their distance from the central area.

7. The apparatus as claimed in claim 1, characterized in that the plurality of means for measuring the gamma-ray flux consists of a plurality of single-anode photomultipliers capable of receiving the light signal emitted by the sensor means.

8. The apparatus as claimed in claim 7, characterized in that the number of photomultipliers is four.

9. The apparatus as claimed in claim 1, characterized in that the plurality of means for measuring the gamma-ray flux consists of a multi-anode photomultiplier.

10. The apparatus as claimed in claim 1, characterized in that the means for analyzing the gamma-ray flux are electronic means.

11. The apparatus as claimed in claim 1, characterized in that the means capable of defining the central axis of the apparatus are in the form of at least two coherent light sources generating narrow light beams, the Intersection of which corresponds to the perpendicular at the center of the sensitive area of the apparatus.

12. The apparatus of claim 1 wherein said means for defining the central axis comprises a light rays.

* * * * *

UNITED STATES PATENT AND TRADEMARK OFFICE
CERTIFICATE OF CORRECTION

PATENT NO.   : 6,603,124 B2
DATED        : August 5, 2003
INVENTOR(S)  : Maublant It is certified that error appears in the above-identified patent and that said Letters Patent is hereby corrected as shown below:

<u>Column 8,</u>
Line 42, delete the word "Intersection" and insert the word -- intersection --

Signed and Sealed this

Seventh Day of October, 2003

JAMES E. ROGAN
*Director of the United States Patent and Trademark Office*